(12) United States Patent  (10) Patent No.: US 8,353,832 B2
Lacoste  (45) Date of Patent: Jan. 15, 2013

(54) SYSTEMS AND METHODS FOR ULTRASOUND TREATMENT OF THYROID AND PARATHYROID

(75) Inventor: Francois Lacoste, Paris (FR)

(73) Assignee: Theraclion, Paris (FR)

( * ) Notice: Subject to any disclaimer, the term of this patent is extended or adjusted under 35 U.S.C. 154(b) by 382 days.

(21) Appl. No.: 12/364,916

(22) Filed: Feb. 3, 2009

(65) Prior Publication Data

US 2010/0094178 A1 Apr. 15, 2010

Related U.S. Application Data (63) Continuation-in-part of application No. 12/251,175, filed on Oct. 14, 2008.

(51) Int. Cl.
A61B 8/00 (2006.01)
(52) U.S. Cl. ........................................................ 600/437
(58) Field of Classification Search ....... 601/2; 600/437
See application file for complete search history.

(56) References Cited

U.S. PATENT DOCUMENTS

| 4,370,983 | A | * | 2/1983 | Lichtenstein ................. 600/301 |
| 5,419,327 | A | | 5/1995 | Rohwedder |
| 5,720,286 | A | | 2/1998 | Chapelon |
| 5,949,080 | A | | 9/1999 | Ueda et al. |
| 6,066,123 | A | * | 5/2000 | Li et al. ........................... 604/507 |
| 6,076,005 | A | | 6/2000 | Sontag et al. |
| 6,097,984 | A | | 8/2000 | Douglas |
| 6,398,731 | B1 | | 6/2002 | Mumm et al. |
| 6,484,053 | B2 | | 11/2002 | Leelamanit et al. |
| 6,488,626 | B1 | | 12/2002 | Lizzi et al. |
| 6,517,492 | B2 | | 2/2003 | Koblanski |
| RE38,030 | E | | 3/2003 | Chapelon |
| 7,171,257 | B2 | | 1/2007 | Thomson |
| 7,318,805 | B2 | | 1/2008 | Schweikard et al. |
| 7,585,296 | B2 | | 9/2009 | Edwards |
| 2001/0012387 | A1 | | 8/2001 | Polz |
| 2002/0193685 | A1 | | 12/2002 | Mate et al. |
| 2004/0015104 | A1 | | 1/2004 | Goldberger et al. |
| 2004/0030268 | A1 | * | 2/2004 | Weng et al. ..................... 601/2 |
| 2004/0122311 | A1 | | 6/2004 | Cosman |
| 2005/0027333 | A1 | | 2/2005 | Lennox |
| 2005/0187495 | A1 | | 8/2005 | Quistgaard et al. |
| 2006/0079764 | A1 | | 4/2006 | Wright et al. |

(Continued)

FOREIGN PATENT DOCUMENTS

WO 2006/129045 12/2006

(Continued)

OTHER PUBLICATIONS

Nederkoorn et al., Recording of Swallowing Events Using Electromyography as a Non-Invasive Measurement of Salivation, Appetite 1999, 33(3), pp. 361-369.

(Continued)

Primary Examiner — Brian Casler
Assistant Examiner — Saurel J Selkin
(74) Attorney, Agent, or Firm — Shoemaker and Mattare (57) ABSTRACT

A treatment device and methods for HIFU treatment of thyroid and parathyroid disorders are provided. The treatment method includes steps of identifying a treatment zone and directing high intensity focused ultrasound energy towards the treatment zone. The treatment device has a first sensor for detecting swallowing motion and a second sensor for tracking the motion of the thyroid and parathyroid tissue with ultrasound imaging.

19 Claims, 8 Drawing Sheets

U.S. PATENT DOCUMENTS

| | | |
|---|---|---|
| 2006/0100509 A1 | 5/2006 | Wright et al. |
| 2006/0203615 A1 | 9/2006 | Gal et al. |
| 2006/0217793 A1 | 9/2006 | Costello |
| 2006/0241443 A1 | 10/2006 | Whitmore, III et al. |
| 2006/0241446 A1 | 10/2006 | White et al. |
| 2006/0282010 A1 | 12/2006 | Martin et al. |
| 2006/0293598 A1* | 12/2006 | Fraser .......................... 600/439 |
| 2007/0055155 A1 | 3/2007 | Owen et al. |
| 2007/0129631 A1 | 6/2007 | Ma et al. |
| 2007/0161894 A1 | 7/2007 | Zdeblick et al. |
| 2007/0270687 A1 | 11/2007 | Gardi et al. |
| 2007/0276244 A1 | 11/2007 | Sui |
| 2008/0030457 A1 | 2/2008 | Schneider |
| 2009/0041854 A1* | 2/2009 | Markert ........................ 424/580 |

FOREIGN PATENT DOCUMENTS

| | | |
|---|---|---|
| WO | 2006/129047 | 12/2006 |

OTHER PUBLICATIONS

Wehrmann et al., Shock Wave Treatment of Salivary Duct Stones: Substantial Progress with a Minilithotripter, Clinical Investigator, 72, pp. 604-608, 1994.

Esnault et al., High Intensity Focused Ultrasound (HIFU) Ablation Therapy for Thyroid Nodules, Thyroid, Ultrasound and Ultrasound Guided FBA, pp. 219-236, Springer, May 2008.

* cited by examiner

SYSTEMS AND METHODS FOR ULTRASOUND TREATMENT OF THYROID AND PARATHYROID

This application is a continuation-in-part of copending application Ser. No. 12/251,175, filed Oct. 14, 2008.

FIELD OF THE INVENTION

The present invention is generally directed to devices and methods for synchronizing ultrasound therapy, and in some embodiments, High Intensity Focused Ultrasound (HIFU) pulse delivery, in some embodiments with movements of a patient undergoing treatment directed to thyroid and parathyroid tissue (for example). Such movements may include, for example, swallowing.

BACKGROUND OF THE INVENTION

The use of ultrasound, including high intensity focused ultrasound (HIFU) for therapeutic purposes has received significant attention in the medical community. During treatment, a portion of the mechanical energy from these high intensity sound waves is converted at the targeted location into thermal energy. The amount of thermal energy convened can be sufficiently intense to cauterize tissue, or to cause tissue necrosis (by inducing a temperature rise to beyond 70° C.). Importantly, the focal point of this energy deposition can be tightly controlled so as to obtain tissue necrosis in a small target area without damaging adjoining tissue. Thus, both benign and malignant tumors can be destroyed with HIFU without surgical exposure to the tumor site.

A particular advantage of HIFU therapy over certain traditional therapies is that HIFU is less invasive. Further advantages include reduced blood loss, reduced risk of infection, shorter hospital stays, and lower health care costs. HIFU has the potential to provide an additional treatment methodology consistent with this trend by offering a method of non-invasive surgery. For example, HIFU enables transcutaneous tumor treatment without making a single incision, thus avoiding blood loss and the risk of infection and with few side effects. Furthermore, HIFU therapy may be performed without the need for general anesthesia, thereby reducing surgical complications and cost. Most importantly, these treatments may be performed on an outpatient basis, further reducing health care cost, while increasing patient comfort.

The application of HIFU for the destruction of benign and malignant tumors in the neck area presents a relatively new direction in the field. Patients with thyroid and parathyroid tumors stand to benefit significantly from relatively non-invasive nature of HIFU. Further, among benign conditions of the neck area, thyroid nodules are frequently discovered during routine physical examination or during investigations for other purposes. Recently, systematic ultrasonographic exploration of a French large adult cohort indicated that 14.5% of subjects had nodular thyroid structures (Valeix el al. (2001), Ann Endocrinol (Paris) 62(6):499-506.) In the United States, 40% of the female population age 50 or older are presented with thyroid nodules at ultrasonography, and the prevalence of thyroid nodules increases throughout life. Patients presenting with such benign nodules are subject to long follow-up procedures and the best therapeutic strategy after the discovery of such nodules is still a matter of debate. Often, the goal of the physician becomes avoiding surgery and choosing among minimally invasive treatments which may be done in an ambulatory settings and result in fewer sides effects compared to surgery.

HIFU is a promising non-invasive procedure for treatment of the disorders of the neck tissue. However, the enduring problems of HIFU application remain in accurately assessing, targeting and monitoring ablated tissues during the therapeutic treatment. Specifically, application of HIFU to the wrong tissue in the neck of a patient can lead lower treatment efficacy and to various side effects, such as for example loss of voice, due to damaging the laryngeal nerves. Thus, in an attempt to circumvent the deficiencies in the art, there have been devices developed to attempt synchronization of HIFU energy with the movements of patients.

U.S. Reissued Pat. No. RE38.030 teaches a method of applying focused ultrasound to the thyroid of a patient. The method includes monitoring the movement of the patient during the focused ultrasound treatment, particularly at the trachea. Echo location is used to determine the position of a portion of the patient's body to identify a treatment zone. If a change in position is detected, an alarm signal is triggered and the position of the therapy device is changed. Thereby, the therapy on the thyroid is continued as the focused ultrasound is kept targeted on the thyroid.

RE38.030 is understood not specifically to disclose, teach or suggest movements in relation to swallowing, nor is it understood to disclose, teach or suggest a separate sensor for the detection of movement of the larynx. Moreover, RE38,030 also appears not to specifically disclose, teach or suggest the stoppage of signal from the focused ultrasound therapy device in response to patient movement including swallowing.

U.S. Pat. No. 6,076,005 is understood to be directed toward gating of therapeutic energy including sonic energy based on the respiratory cycle of the patient. The patient's lungs are monitored to provide quasi-continuous measurements of the actions of the patient's lungs. However, U.S. Pat. No. 6,076,005 is understood not to disclose, teach or suggest movements in relation to swallowing, nor does it teach a separate sensor for the detection of movement of the larynx. Further, U.S. Pat. No. 6,076,005 is also understood not to disclose, teach or suggest the stoppage of signal from the focused ultrasound therapy device in response to patient movement including swallowing.

Thus, there is understood a general need in the art to provide HIFU devices capable to deliver therapeutic energy to the correct tissue i.e. the thyroid or parathyroid, despite the movement of the tissue of the neck due to patient's swallowing or other movement during treatment.

SUMMARY OF THE INVENTION

The foregoing and other features, aspects, and advantages of the present invention will be more apparent from the following detailed description, which illustrates exemplary embodiments of the present invention.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the drawings, subsequent detailed description and appended claims. In some embodiments, the invention provides an ultrasound therapeutic treatment device comprising a first sensor for detecting at least one of neck motion, throat/neck motion and swallowing motion in a subject; a second sensor for detecting a thyroid and/or parathyroid in the subject, a high intensity focused ultrasound (HIFU) pulse generator and controlling means for controlling the HIFU pulse generator based on signals from at least one of the first sensor and the second sensor.

In some embodiments, the treatment device may comprise a controlling means for controlling various aspects of the method and/or system/device, such means may include a micro processor or the equivalent thereof. In some embodiments, when the first sensor detects movement of a patient, the controlling means stops pulse generation from the HIFU pulse generator. Preferably the first sensor is positioned on the larynx of the patient. In some embodiments, when the second sensor detects a change in position of a tissue in the patient from a first position to a second position, the controlling means adjusts the HIFU generator such that at least one HIFU pulse is focused on the tissue in the second position. Preferably the tissue is parathyroid and/or thyroid tissue. Optionally the second sensor is an ultrasonic scanning probe.

In some embodiments, the first sensor is selected from the group consisting of a strain gauge, a laser to measure distance, an electromyography sensor, and a combination of any of the foregoing.

In some embodiments, a method for treating disorders of thyroid and/or parathyroid with HIFU in a subject in need thereof is provided and may comprise positioning a first sensor to detect at least one of neck motion, throat motion and swallowing motion, in the subject; positioning a second sensor to detect a position of a thyroid and/or parathyroid in the subject; positioning a HIFU pulse generator to provide at least one HIFU pulse to the subject; and controlling the HIFU pulse generator to cease HIFU pulses upon the first sensor detecting motion. Preferably, the second sensor is positioned sagitally i.e. parallel to the neck of the patient.

In some embodiments, the above noted method may further comprise providing at least one of controlling means for controlling the HIFU pulse generator and synchronizing means for synchronizing a signal from at least one of the first sensor and the second sensor with the HIFU pulse generator.

The above-noted method may further comprise detecting a change in position of the parathyroid and/or thyroid from a first position to a second position and adjusting the HIFU generator such that at least one HIFU pulse is focused on the parathyroid and/or thyroid in the second position.

The above-noted method may further comprise selecting the first sensor from the group consisting of a strain gauge, a laser to measure distance, an electromyography sensor and a combination of any of the foregoing.

In some embodiments, the method relates to the disorders of the thyroid and parathyroid selected form the group consisting of thyroid nodules, hyperthyroidism, primary or secondary hyperparathyroidism, thyroid cancer, parathyroid cancer and any combination of the foregoing.

In some embodiments, an ultrasound therapeutic treatment device/system is provided which may include a first sensor for detecting at least one of neck motion, throat motion and swallowing motion in a subject; a second sensor for detecting a thyroid and/or parathyroid in the subject; a high intensity focused ultrasound pulse (HIFU) generator; a micro processor for controlling the HIFU pulse generator based on signals from at least one of the first sensor and the second sensor. According to this embodiment, when the first sensor detects motion, the controlling means stops pulse generation from the HIFU pulse generator.

The second sensor may be used to detect a change in position of the parathyroid and/or thyroid from a first position to a second position. In such embodiments, the controlling means adjusts the HIFU generator such that a HIFU pulse is focused on the parathyroid and/or thyroid in the second position.

In some embodiments, a method for treating disorders of thyroid and/or parathyroid with HIFU in a subject in need thereof is provided and may include positioning a first sensor to detect at least one of neck motion, throat motion and swallowing motion in the subject, positioning a second sensor to detect a position of a thyroid and/or parathyroid in the subject; providing a HIFU pulse generator to provide at least one HIFU pulse to the subject. Furthermore, at least one of controlling means for controlling the HIFU pulse generator and synchronizing means for synchronizing a signal from at least one of the first sensor and the second sensor with the HIFU pulse generator are provided which in turn control the HIFU pulse generator to cease HIFU pulses upon the first sensor detecting motion.

The above-noted method may relate to detecting a change in position of the parathyroid and/or thyroid from a first position to a second position and adjusting the HIFU generator such that at least one HIFU pulse is focused on the parathyroid and/or thyroid in the second position.

Moreover, the above-noted method may relate to disorders of the thyroid and parathyroid selected form the group consisting of thyroid nodules, hyperthyroidism, primary or secondary hyperparathyroidism, thyroid cancer, parathyroid cancer and any combination of the foregoing.

In some embodiments, methods of the present invention may be used to treat and/or alleviate the symptoms of thyroid nodules, hyperthyroidism, primary or secondary hyperparathyroidism, thyroid cancer or parathyroid cancer and other known thyroid and parathyroid disorders.

Parathyroid glands are four pea-sized glands located just behind the thyroid gland in the front of the neck. Hyperparathyroidism is an overactivity of one of the four parathyroid glands resulting in excess production of parathyroid hormone (PTH), also called parathyroid hormone. The parathyroid hormone regulates calcium and phosphate levels and helps to maintain these levels. Overactivity of one or more of the parathyroid glands causes high calcium levels (hypercalcemia) and low levels of phosphate in the blood. Primary hyperparathyroidism, also called Parathyroid-related hypercalcemia, results from a hyperfunction of the parathyroid glands themselves. There is oversecretion of PTH due to adenoma, hyperplasia or, rarely, carcinoma of the parathyroid glands. About 90 percent of all cases of hyperparathyroidism are caused by an adenoma. The tumors seldom are cancerous. They will grow to a much larger size than the parathyroid glands, often to the size of a walnut. Genetic disorders or multiple endocrine tumors also can cause a parathyroid gland to enlarge and oversecrete hormone. In 10 percent or fewer of patients with primary hyperparathyroidism, there is enlargement of all four parathyroid glands. Usually, only one of the four parathyroid glands is affected. Secondary hyperparathyroidism is the reaction of the parathyroid glands to a hypocalcemia caused by something other than a parathyroid pathology, e.g. chronic renal failure.

So far symptomatic patients usually are sent for surgery to remove the parathyroid tumor (parathyroid adenoma). Most experts believe that almost all patients with hyperparathyroidism should be evaluated for surgery.

Diagnosis of hyperparathyroidism most often is made when a blood test (radioimmunoassay) reveals high levels of parathyroid hormone and calcium and low or variable phosphorous levels. A blood test that specifically measures the amount of parathyroid hormone has made diagnosis simpler.

In some embodiments, methods of the present invention may be used to treat primary or secondary hyperparathyroidism comprising identifying a treatment zone to which ultrasonic energy should be applied to and directing high intensity focused ultrasound energy towards the treatment zone.

During the treatment either one or more of the parathyroid glands can be treated.

High Intensity Focused Ultrasound (HIFU) is a process that allows the delivery of a large amount of heat energy to a confined space. For example the width of focus (6 dB) at 3 MHz, could be 0.84×0.42×1.5 mm (cross×cross×along axis). Thus applying High Intensity Focused Ultrasound (HIFU) is especially appropriate for small structures such as parathyroid glands. This holds even more since parathyroids are located very close to sensitive structures, such as the trachea and the recurrent laryngeal nerve.

Parathyroids are usually located deeper from the skin than for example the thyroid. Typically they are located in a tissue depth of 15-35 mm. However most parathyroids can be reached with the focus being arranged in a distance of for example 24.5 mm from the rim of the treatment unit.

The treatment area may be located precisely with an external ultrasound applicator. Ultrasound imaging provides high resolution imaging of parathyroid and is better in that respect than MRI or Scanner. Parathyroids are usually hypoechoic and located behind the thyroid. Alternatively isotope scans or fine needle aspiration can be used to confirm parathyroid status. Sensitive structures (trachea, vessels) are also visible by ultrasound.

The image array, for example a 7.5 MHz-12 MHz 128 element imaging linear array, is located in the centre of the treatment transducer thus allowing constant, real-time imaging of the tissue being treated. The treatment unit may have an external diameter of 60 mm, an active diameter of 56 mm, and a width of inactive area of 14.5 mm.

The fixed position of the array with respect to the firing transducer ensures that the acoustic energy is delivered in a precise, predictable position. The ultrasound images accurately image the tissue to be treated. The energy deposition of the device hence directly corresponds to the areas identified on those ultrasound images.

Preferably the combined visualization and treatment unit (VTU) is rotatable on its axis and thus be able to display two planes of imaging, providing the operator with a 3D representation of the target and its surrounding.

In a preferable embodiment of the invention a representation of the acoustic HIFU cone is overlaid on the ultrasonic image, thus indicating the exact position of the focus. During treatment, the tissue under treatment preferably is continuously monitored by ultrasound. Furthermore the ultrasonic image of the tissue taken during the targeting phase may be displayed for reference. The outlines of the target, skin, carotid and trachea are overlaid over the live image by the operator. These two features allow the operator to continuously verify that position of the visualization and treatment unit is correct. Should there be an offset, the operator can easily reposition the visualization and treatment unit to the correct position.

The HIFU energy is adjusted to each individual patient using an algorithm whereby starting from a low level, the VTU being in a fixed position pointing to the centre of the parathyroid, the pulse energy is gradually increased until hyperechoic marks appear on the ultrasonic real time image.

During treatment, especially during treatment of hyperparathyroidism, the patient advantageously lay on a treatment couch in supine position, the neck in hyperextension to facilitate access to the target. This position should be kept during the estimated duration of the procedure, about 30 minutes.

The operator covers the patient skin with a thin layer of ultrasonic gel over the treatment area. The operator places the VTU so that the center of the target, especially the enlarged parathyroid gland, is approximately centered laterally, and moves the VTU up or clown to place marks indicating the focus on the image of the target. By rotating the VTU on itself, the centering is performed both transversally longitudinally.

The focal point is centered on the outlined target.

The pulse acoustic energy applied to the treatment area is the product of acoustic power by the duration of the pulse. The acoustic power is the electric power to the transducer time the electro-acoustic efficiency of the transducer. In practice the maximum acoustic power is 70 W.

The reference power being the acoustic power that reaches the focus when the VTU is in water is for example set at 15.3 W per default. The reference pulse duration is set at 6 s per default. The reference pulse energy is thus 92J.

The first pulse is delivered to the tissue using the reference energy, corrected for depth. The emitted power P is corrected as a function of target depth to take into account part of the ultrasonic absorption of the tissue superficial to the focal zone, according to the formula:

$$P = P_{ref} * \exp(2 * \mu * F * D)$$

Where:
$P_{ref}$: reference power in Watts: for example 15.3 Watt per default but adjustable by the operator
The term exp( ) takes into account some of the acoustic power lost by the beam in the superficial tissues before reaching the focus.
F: Ultrasound frequency expressed in MHz (fixed value set to 3 MHz).
D: Target depth, i.e. distance between the skin to the focal point, expressed in cm
µ: Tissue acoustical absorption expressed in Neper/cm/MHz. The exact value is unknown as it depends on the tissue type and each individual. A low value of 0.07 Neper/cm/MHz was chosen to minimize risk of over exposing the target.

For example if the depth is 20 mm, which is a typical distance of a parathyroid to the skin, the total acoustic energy of the pulse will be of: 6 s×35.45 W=213 J. And at the lesion depth, the residual energy that has not been absorbed by the tissues is of 92 joules. For safety reasons, the reference pulse energy is limited to 281 J/pulse.

Depending on the acoustic intensity of the transducer, there are two phenomena leading to tissue destruction, respectively to a ablation of parathyroid, with HIFU. At intermediate intensities greater than 500 Watt/cm$^2$ and less than 3000 Watt/cm$^2$, HIFU energy may produce cavitation bubbles near the focus. This, in turn, enhances the absorption of the tissue medium and helps transforming the incoming ultrasonic energy into heat. This phenomenon is also responsible for the position of the lesion ahead of the focal point (i.e. towards the transducer). In the focal zone the temperature rises because the acoustic waves produce heat by acoustic absorption of the tissue. Each pulse creates a small "lesion" of coagulation. The tissue may reach boiling temperature. The heat builds up at the focus where the energy is concentrated. Where the energy is not concentrated (i.e. before and after focus) the temperature is regulated by blood flow and there is no residual effect on tissue.

A HIFU treatment, especially the treatment of parathyroidism, consists of repeated pulses, placed adjacent to one another in order to cover the whole target. The number of pulses varies between 5 and several hundred. The motion pattern is for example an outward spiral from centre. The spacing between the lesions in the motion pattern is for example 1.2 mm. The pause between two pulses must be long enough so as to let the skin cool before the next pulse is emitted.

As some heat is deposited in the tissue located before the focal point ("pre-focal heating"), the tissue, especially the skin tissue, should be kept on normal temperature. Therefore cooling may be provided by the VTU. In operation the VTU is preferably covered by a thin balloon made of silicon material, effectively creating a liquid-filled chamber in front of the transducer. The fluid for example is water with 10 grams Polyvinylpyrrolidone (PVP) per 1 litre and methylene blue, which helps the operator to check that the cooling circuit is properly filled. The fluid maybe originally stored in a pouch inserted in the cooler located in the Electronics Cabinet. Preferably the fluid is circulated in a closed circuit between the pouch and the VTU by the pumps. Two temperature sensors located in the VTU ensure that the fluid in the VTU is properly cooled to 10° C. and a pressure sensor, also located in the VTU, ensures that the pressure of the balloon is constant over the patient skin.

To reduce prefocal heating or skin burn, the pauses between the HIFU pulses preferably are chosen such as to allow for that tissue to return to normal temperature. In the treatment of the parathyroid gland, the pauses between the pulses are instrumental in eliminating the risk of skin burns. Accordingly, the pulse repetition is limited by the capacity of the skin to withstand repetitive high acoustic power pulses. It has been determined experimentally that the average intensity should not exceed 2.5 W/cm² at 3 MHz.

The pauses toff can be determined according to the following formula.

$$toff = \frac{F \cdot AcousticPower \cdot ton}{SkinTol \cdot \left[ TxdArea \cdot \left( \frac{TissueDepth}{FocusToRim} \right)^2 \right]} - ton$$

Where:
ton=pulse duration in seconds
F: acoustic frequency in MHz
Acoustic power=3 MHz acoustic power that is delivered by the transducer during the HIFU pulse. Value expressed in Watts.
TissueDepth: Thickness of tissues to go through, from the skin to the focal point over the lesion to be treated. Value expressed in mm.
FocustoRim: This is the distance from the focal point to the border of the active surface of the transducer projected over the ultrasound axis. This value is expressed in mm.
TxdArea: This is the cross section area of the transducer projection on the skin. This value is expressed in cm².
SkinTol: This is the allowable average acoustic intensity through the skin. This value is expressed in W×MHz/cm². The value has been determined experimentally (see above) to 2.5 W/cm² at 3 MHz. If the acoustic frequency is 1 MHz, then Iskin should not exceed 7.5 W/cm².

The treatment can be performed again if necessary. Preferably a treatment is repeated at least twice, at least one week apart, focussed either at the same tissue site or at a tissue sites separated by 1 mm to 1 cm from the previously treated treatment zone.

In an advantageous embodiment of the invention the method treating hyperparathyroidism further comprises the step of measuring the blood levels of parathyroid hormone and/or calcium and/or phosphorus. By monitoring the values of at least one blood level the effect of the treatment may be controlled.

Additionally or alternatively the blood levels of TSH, T3 and/or T4 hormones may be monitored.

Preferably a repeat course of treatment is applied depending on values of the blood level and/or on the course of the blood levels of parathyroid hormone and/or calcium and or phosphorus. For example no further treatment is necessary if a certain blood level decreases or increases beyond a predetermined value or if a certain blood level decreases or increases by more than a predetermined amount or percentage after a predetermined time interval.

In some embodiments, methods of the present invention may be used for of ablating a parathyroid comprising the steps of comprising identifying a treatment zone to which ultrasonic energy should be applied to, said treatment zone including at least a part of the parathyroid, and directing high intensity focused ultrasound energy towards the treatment zone.

In some embodiments, an ultrasound therapeutic device is provided which may comprise a sensor for detecting a parathyroid in the subject and a high intensity focused ultrasound (HIFU) pulse generator, wherein said high intensity focused ultrasound (HIFU) pulse generator is operable such that it provides a focal zone being located in a treatment zone including at least a part of the parathyroid.

Other objectives and advantages of the present invention will become obvious to the reader and it is intended that these objectives and advantages are within the scope of the present invention.

To accomplish the above and related objectives, this invention may be embodied in the form illustrated in the accompanying drawings, attention being called to the fact, however, that the drawings are illustrative only, and that changes may be made in the specific construction illustrated.

BRIEF DESCRIPTION OF THE DRAWINGS

For a better understanding of the present invention, reference is made to the following description, taken in conjunction with the accompanying drawings, in which like reference characters refer to like parts throughout, and in which.

DETAILED DESCRIPTION

It is noted that in this disclosure and particularly in the claims and/or paragraphs, terms such as "comprises," "comprised," "comprising," and the like can have the meaning attributed to it in U.S. patent law; that is, they can mean "includes," "included," "including," and the like, and allow for elements not explicitly recited. These and other embodiments are disclosed or are apparent from and encompassed by, the following description.

The terms "HIFU pulse generator," as used herein and in the claims that follow all refer to a HIFU transducer that is capable of being energized to produce ultrasonic waves that are much more energetic than the ultrasonic pulses produced by an imaging transducer, and which can be focused or directed onto a discrete location, such as a treatment site in a target area.

The terms "HIFU treatment" as used herein refer to a treatment comprising (i) identifying a treatment zone to which ultrasonic energy should be applied to, said treatment zone including at least a part of the parathyroid and (ii) directing high intensity focused ultrasound energy towards said treatment zone, wherein a HIFU pulse generator provides at least one HIFU pulse to the subject.

In this respect, before detailing at least one embodiment of the invention, it is to be understood that the invention is not limited in its application to the details of construction and to the arrangements of the components set forth in the following description or illustrated in the drawings. The invention is capable of other embodiments and of being practiced and carried out in various ways where particular configurations, process steps, and materials disclosed herein as such configurations, process steps, and materials may vary somewhat. In addition, it is to be understood that the phraseology and terminology employed herein are for the purpose of the description and should not be regarded as limiting. Furthermore, as will be apparent to those skilled in the art, the present invention may be embodied in other specific forms without departing from the essential characteristics thereof.

Figure 1:
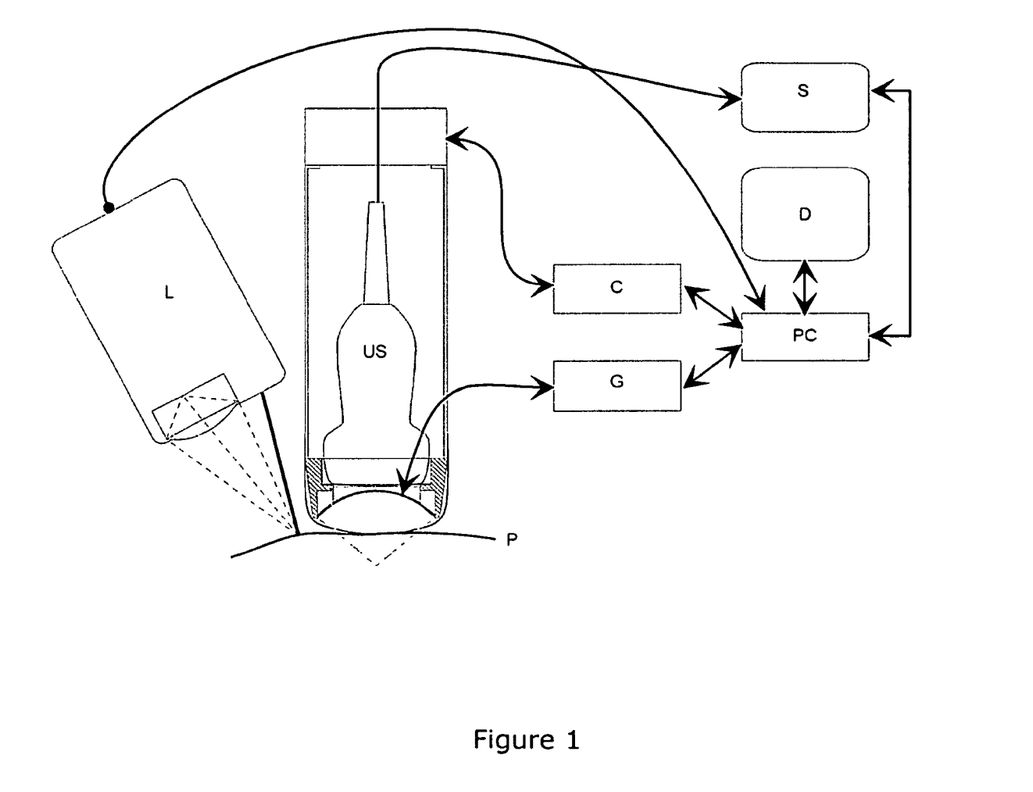
FIG. 1 is an overall diagrammatic view of a complete treatment device that is suitable for incorporating the first and second sensors of the invention according to some embodiments.

For purposes of the description of the drawings and the embodiments of the present invention, as mentioned for the drawing, FIG. 1 may not be drawn to scale. Some areas drawn may be larger and/or simpler in order to clearly portray the improvement to what has already been established. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed. It is also to be understood that the terminology employed herein is used for the purpose of describing particular embodiments only and is not intended to be limiting since the scope of the present invention will be limited only by the appended claims and equivalents thereof.

Referring now in detail to the drawing, the first and second sensor according to some embodiments of the present invention can be incorporated in a treatment device as shown diagrammatically in FIG. 1. According to this device, the sensors "L" and "US" are associated with a plurality of elements such as, for example, a power generator "G", for powering the treatment means, a displacement controller "C", for displacing the head, an ultrasound scanner "S", connected to the probe, a display screen "D", and a computer "PC" that serves to manage the device. All of the elements of the device including sensors "L" and "US" are connected to the "PC". The elements "US", "G", "C", "PC" "D" and others, are described in detail in related applications WO 2006/129047 and WO 2006/129045 incorporated by reference herein.

The first sensor may be a non contact distance measuring tool "L", such as for example a laser. This is depicted on the left side of the FIG. 1. The way "L" detects motion may be as follows: "L" emits a laser beam which is directed towards the throat of the patient. In other embodiments, the first sensor is placed directly on the patient's larynx.

The light reflected by the patient skin is focused by the lens onto a linear detector (the light follows the dashed lines as shown in FIG. 1). Depending on the position of the focused light on the linear detector, the distance of the skin is calculated. "L" can be a commercial device, such as Model OADM 2014471/S14C from Baumer Electric.

The OADM laser distance sensor may be a self-contained unit designed to accurately measure the distance to a target based on triangulation principal and output the measurement either through an analog and/or a digital interface. The sensors preferably incorporate microprocessor technology to further optimize the dual analog output. The OADM 20 laser distance sensors may utilize a fast microcontroller that enables flexible adaptation of different parameters to the user's requirements. Laser light is available in either a laser beam or a laser beam line configuration depending on the target's surface. These sensors may be equipped with a 90° connector for quick and easy adaptability to the application environment.

In some embodiments, the first sensor may be a strain gauge, and/or may be or include an electromyography sensor.

The second sensor is mostly used to track the motion of the tissues, such as for example thyroid and/or parathyroid with ultrasound imaging. In one embodiment, the imaging means may be ultrasonic imaging probe, in another embodiment, the imaging means may be X-ray probe, and in yet another embodiment, the imaging means may be a Magnetic Resonance Imaging (MRI) device. In another embodiment, the second sensor is an ultrasonic scanning probe. The imaging means achieve representation of the tissue motion in space or in a plane. It is advantageous that the ultrasound array is disposed sagittal to the patient, i.e. parallel to the neck The preferred imaging means according to the instant invention is the ultrasonic probe as designated by "US". This element of the therapeutic device is shown in FIG. 1 and is described in detail in the related applications WO 2006/129045 and WO 2006/129047 which are incorporated by reference herein.

In some embodiments, the synchronizing electronics may be embedded in a computer, "PC" as shown in FIG. 1. The synchronizing electronics may combine the signals from the swallowing sensor with HIFU pulse triggers, such that if swallowing is detected, no pulse is triggered; and/or directing the applicator of HIFU energy to follow the appropriate tissue when the patient moves.

Embodiments of the disclosure provide methods for administering HIFU therapy to treat disorders of thyroid and parathyroid tissue. These include treatment of the benign and malignant thyroid and parathyroid disorders such as for example thyroid nodules, hyperthyroidism, primary and secondary hyperparathyroidism, thyroid and parathyroid cancer and others.

In general, the treatment of the thyroid and parathyroid tissue with an HIFU device takes 10 to 30 minutes in an outpatient clinic. A local anesthetic is administered prior to treatment. The ultrasound energy may be gradually increased until more than 70% of the targeted thyroid or parathyroid tissue is destroyed.

It has been observed that a complete thyroid and/or parathyroid tumor treatment (100% shrinkage) may be obtained. Alternatively, the tumor may be treated in several sessions, with sufficient time between each session for the macrophages in the patient's body to clear away the necrotic tissue resulting from the previous treatment session, thus effectively debriding the treatment side and exposing remaining tumor tissue for the next HIFU therapy session. Several HIFU therapy sessions may be needed to completely eradicate the tumor. Further, the treatment of a benign and/or malignant tumor using a combination of HIFU and drugs, such as for example thyrotropin (TSH) suppressive levothyroxine (LT4) and/or standard chemotherapy drugs, may yield synergistic results, particularly by beginning the HIFU therapy after the maximum benefit of the drug therapy on the tumor and/or nodule has been realized.

Figure 2:
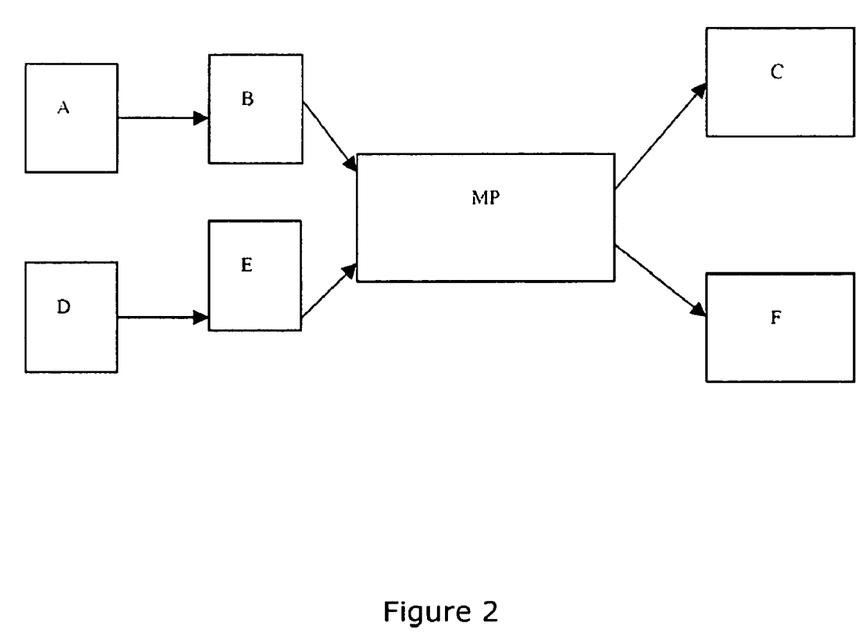
FIG. 2 and FIG. 3 are a flow charts showing the various steps of a method for treating disorders of thyroid and/or parathyroid with HIFU in a subject in need thereof according to some embodiments.

As shown in FIG. 2, when performing the treatment according to the instant method, the subject receiving the treatment periodically swallows (A). Accordingly, the first sensor, which is placed directly on the larynx, may be used to detect such movement (e.g., swallowing) of the subject (B) and then may transmit a signal to the microprocessor (MP) regarding such detected motion. The microprocessor may then signal for the HIFU generator to stop generating pulses during the period of the motion, thereby preventing injury to the subject receiving treatment (C). Concurrently, the subject receiving treatment periodically moves the neck region of the subject undergoing treatment (D). Accordingly, in some embodiments, the second sensor may be used to detect such movement of the subject with the use of imaging means, from a first position to a second position (E), and then transmits a signal regarding this movement to the microprocessor (MP). The microprocessor may then signal the controller (e.g., a microprocessor) of the HIFU generator to reposition the generator to keep the HIFU pulses focused on the thyroid and/or parathyroid of the subject in the second position (F).

Figure 3:
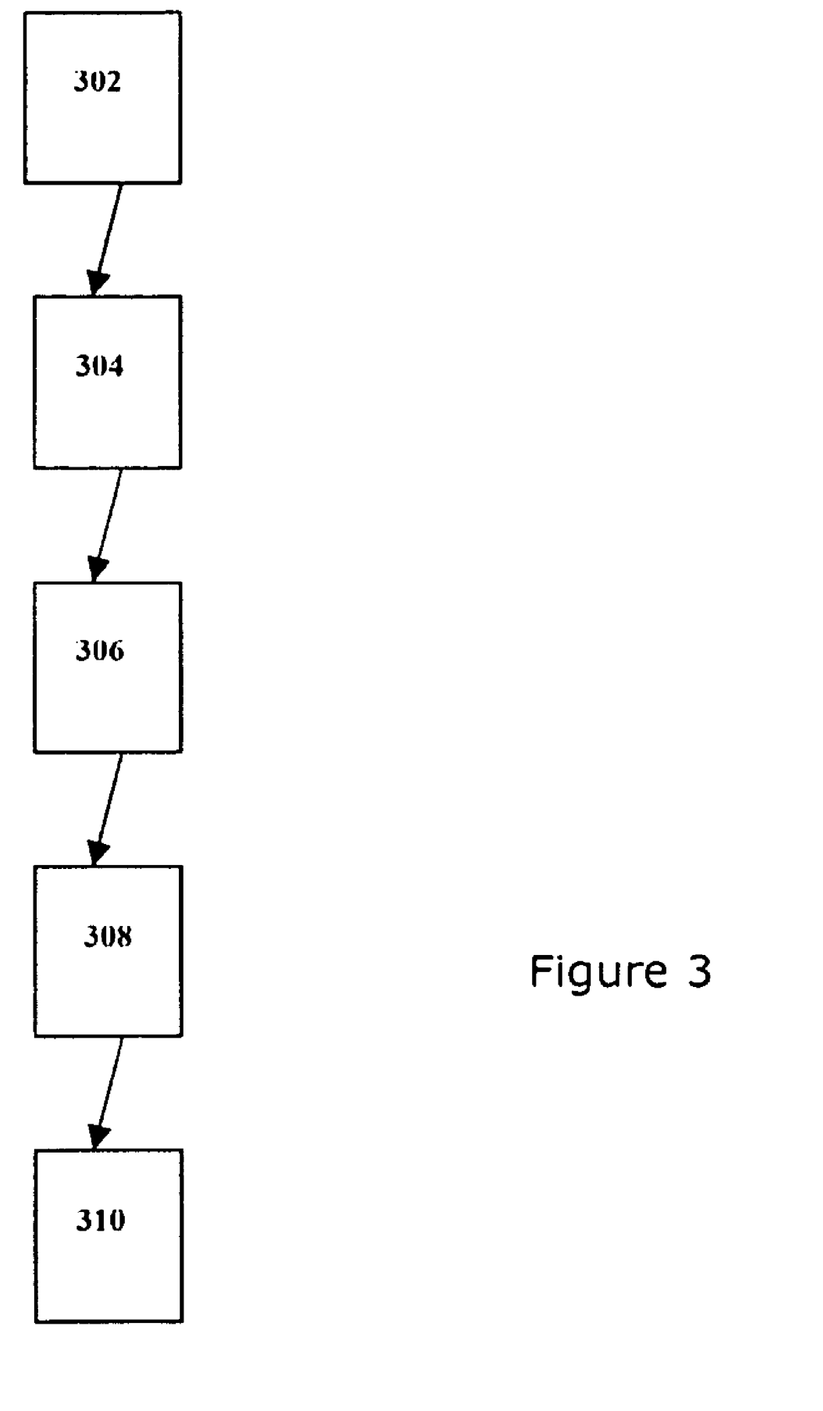

The flow chart shown in FIG. 3 is a diagram outlining the various steps of the method for treating disorders of thyroid and/or parathyroid with HIFU in a subject in need thereof according to some embodiments of the disclosure. Starting at 302, the first sensor is positioned to detect at least one of neck motion, throat motion and swallowing motion. In some embodiments of the instant method, the first sensor is placed directly on the larynx. Then at 304, the second sensor is positioned to detect position of a thyroid and/or parathyroid in the subject. In some embodiments of the instant method, the second sensor is positioned directly on thyroid and/or parathyroid tissue. At 306, the HIFU pulse generator is provided to generate at least one HIFU pulse to the subject. At 308, the controlling means for controlling the HIFU pulse generator are provided. In some embodiments, in addition to controlling means, synchronizing means for synchronizing a signal from at least one of the first sensor and the second sensor with the HIFU pulse generator are provided. Finally at 310, the controlling HIFU generator ceases the HIFU pulses upon the first sensor detecting motion. The synchronizing means may comprise a microprocessor and/or other electronic or software run on a microprocessor (e.g., computer), and may be combined with a microprocessor/computer which comprises the controlling means.

The MP unit controls and, in some embodiments also synchronizes, a signal from at least one of the first sensor and the second sensor with the HIFU pulse generator. Specifically, when first sensor detects at least one of neck motion, throat motion and swallowing motion, it sends a signal to the MP which processes information and in turn sends a signal to HIFU generator to cease HIFU pulses. Similarly, when the second sensor detects the change in position of the thyroid and parathyroid from first position to a second position, it sends a signal to the MP which processes information and in turn sends a signal to the HIFU pulse generator to adjust accordingly, such that for example, at least one HIFU pulse is focused on the parathyroid or thyroid in the second position. Some such embodiments are also summarized in FIG. 4.

Figure 4:
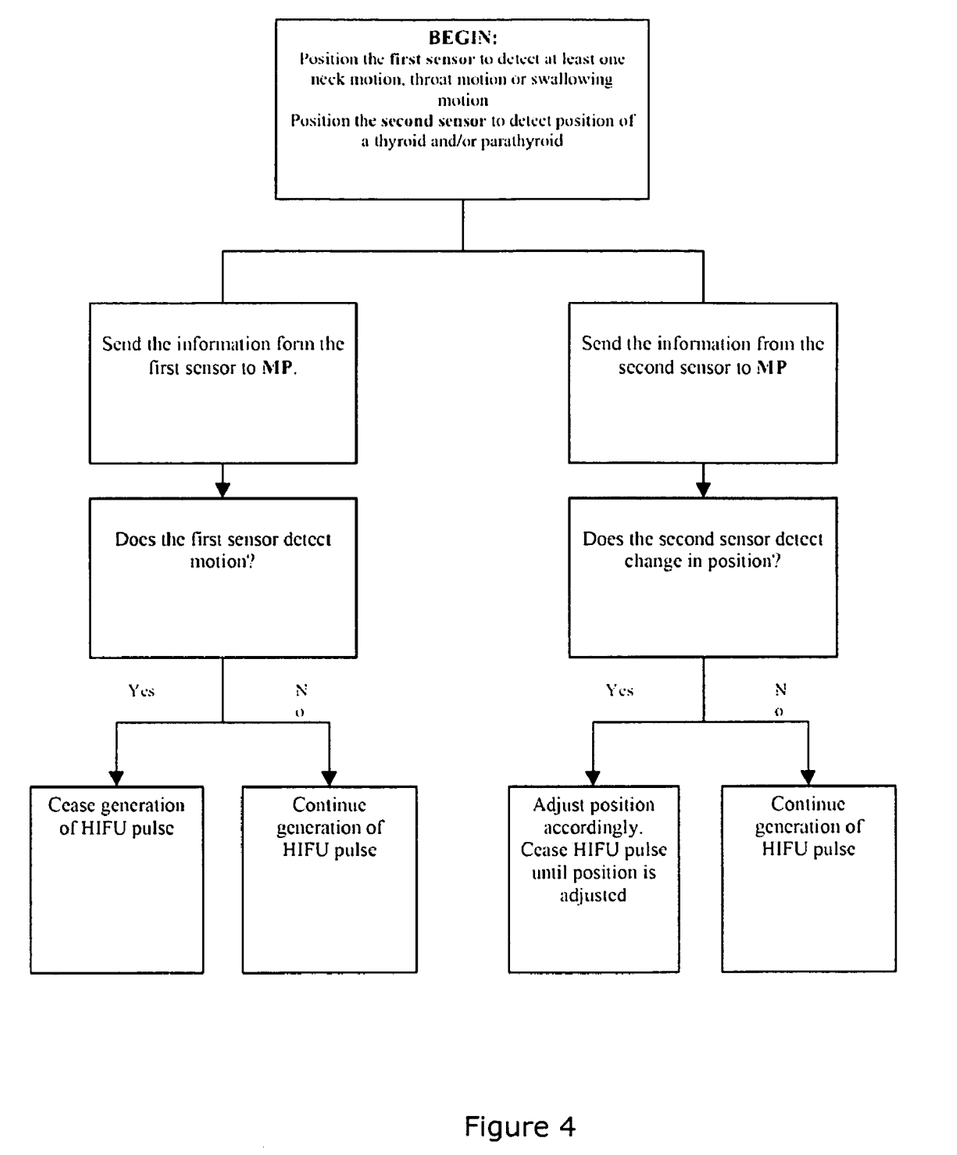
FIG. 4 is a flow chart illustrating steps (for some method embodiments of the present disclosure) followed during use of some apparatus/system embodiments disclosed in the present disclosure.

Specifically, the procedure begins by placing the first sensor to the neck area to detect at least one motion of the neck, throat and/or swallowing motion. If any motion is detected by the first sensor, the signal is send to the MP unit which processes the received information, and further sends the signal to the HIFU generator to cease HIFU pulse. If the first sensor does not detect any motion in the neck area, the signal is send to the MP unit which processes information and further sends the signal to HIFU generator to continue generating at least one pulse.

Similarly, if the second sensor detects a change in the position of the thyroid or parathyroid tissue, the signal is send to the MP which processes the information and further sends the signal to the HIFU generator to cease pulse until the position is adjusted such that the HIFU generator is focused on the thyroid or parathyroid tissue. However, if the second sensor does not detect position of the thyroid or parathyroid, the signal is send to the MP which further sends the signal to the HIFU generator to continue generating at least one pulse. In some embodiments, the signal received from the first sensor and the second sensor is send to the MP and further synchronized with the HIFU pulse generator.

Figure 5A:
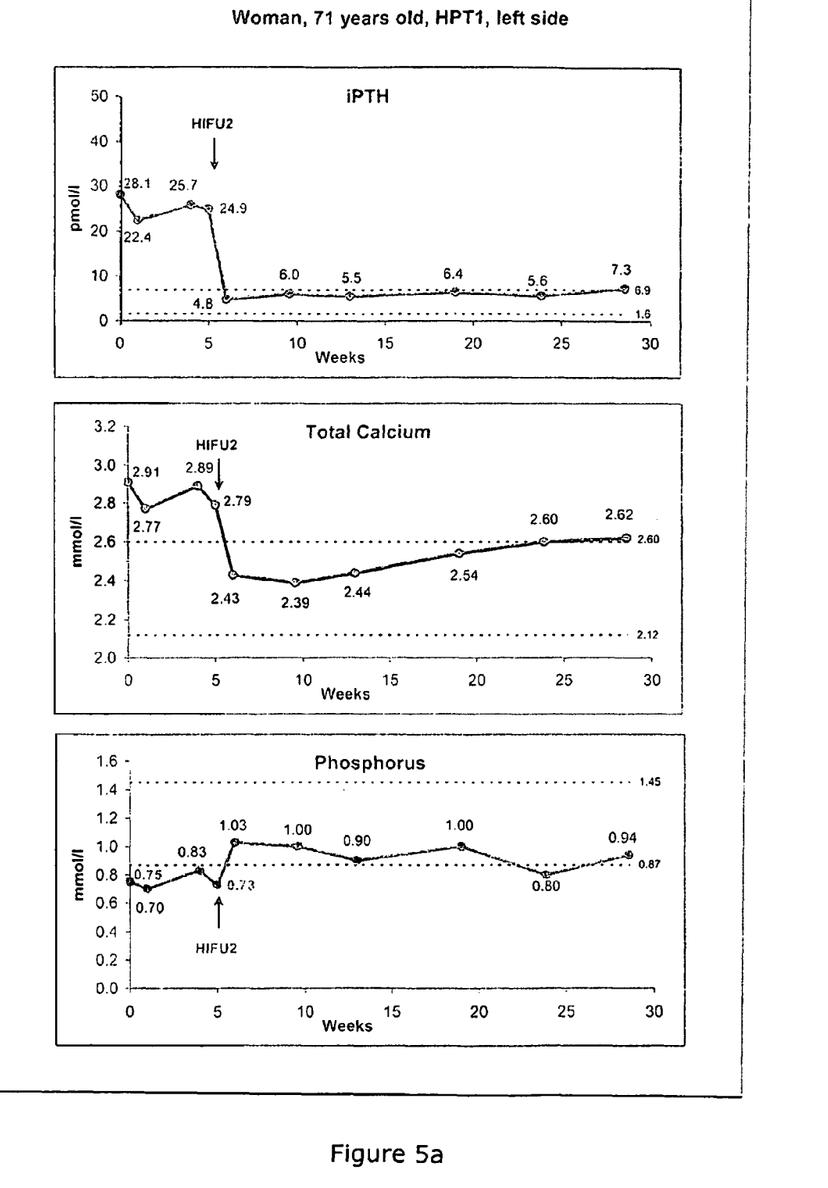
FIGS. 5a and 5b are examples of time dependent courses of blood levels after HIFU treatments.
Figure 5B:
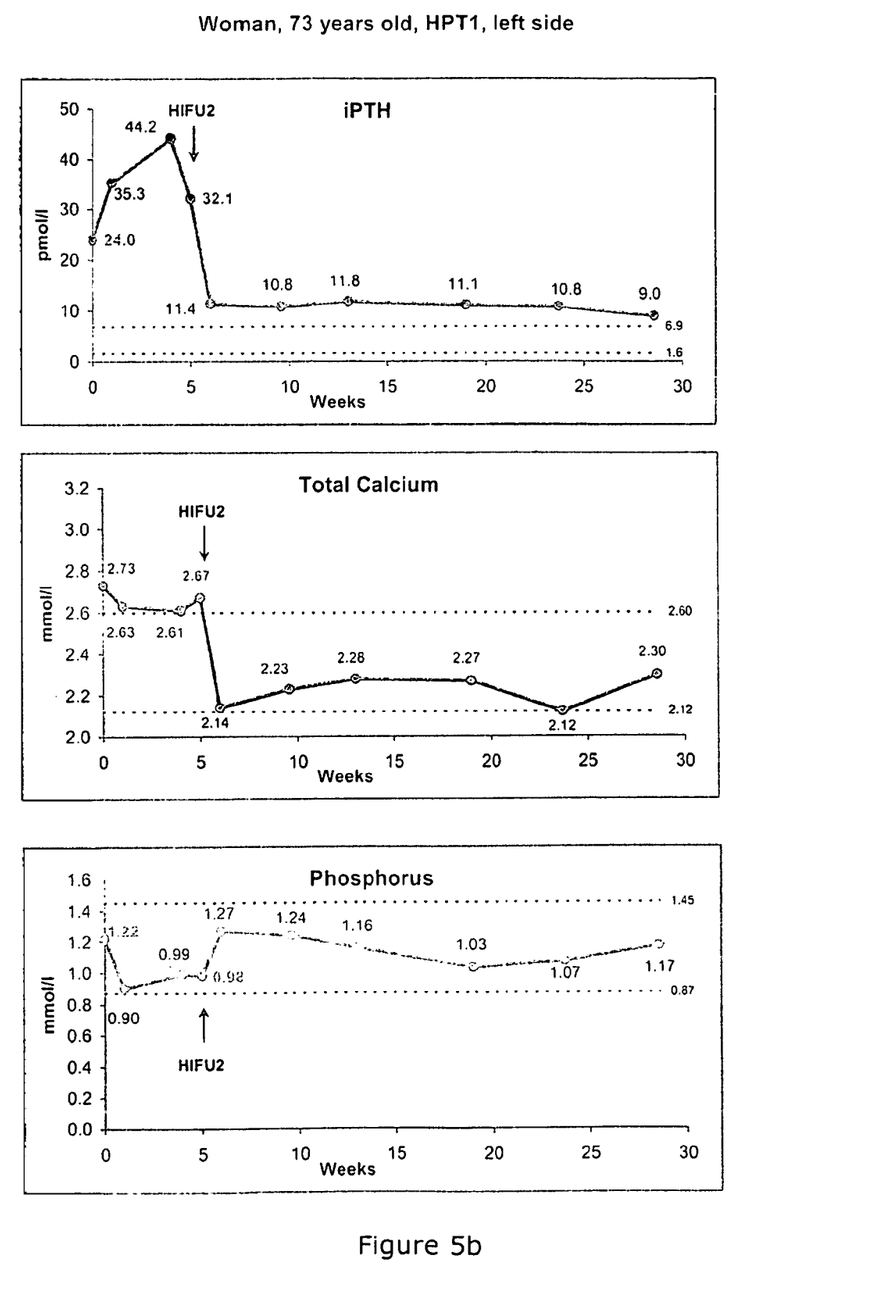

FIGS. 5a and 5b are examples of time dependent courses of blood levels after HIFU treatments for two different patients. Dashed lines show the boundaries of the target values for the respective levels.

FIG. 5a relates to a 71 years old woman with primary hyperparathyroidism in the left side. In a first plotting the figure shows the time dependent course of the parathyroid hormone blood level in pmol/l, in a second plotting the time dependent course of the calcium level in mmol/l and in a third plotting the time dependent course of the phosphorus level in mmol/l is presented.

FIG. 5b is an analogue presentation of second patient, a 73 years old woman with primary hyperparathyroidism in the left side.

The plotting starts after a first HIFU treatment. In both examples parathyroid hormone and calcium levels do not significantly drop after the first treatment. For the second patient the parathyroid hormone level even raises during the first four weeks after the first treatment. In both cases the HIFU treatment is repeated after 5 weeks.

After the second HIFU treatment the blood level of parathyroid hormone and the blood level of calcium significantly decrease, that is by more than 30% with respect to the originally measured value. The long-time behaviour confirms the success of the treatment. Even after 30 weeks after the first treatment (25 weeks after the second HIFU treatment) the blood levels rest on a stable level. A further treatment thus is not necessary.

The third plottings of FIGS. 5a and 5b show the time dependent course of the phosphorus level. The phosphor levels slightly increase after the second treatment, which can give an additional hint to the success of the therapy.

Figure 6:
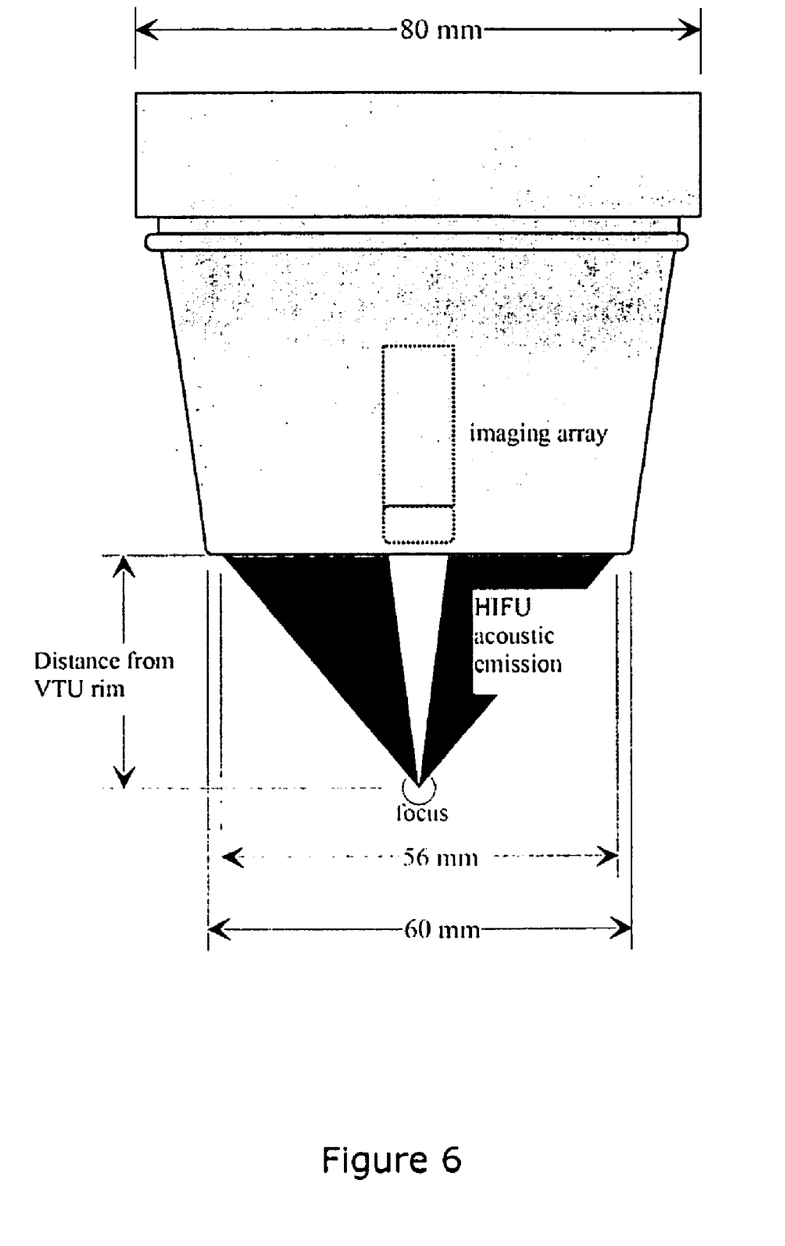
FIGS. 6 and 7 schematically show a visualization and treatment unit (VTU) according to the present invention.
Figure 7:
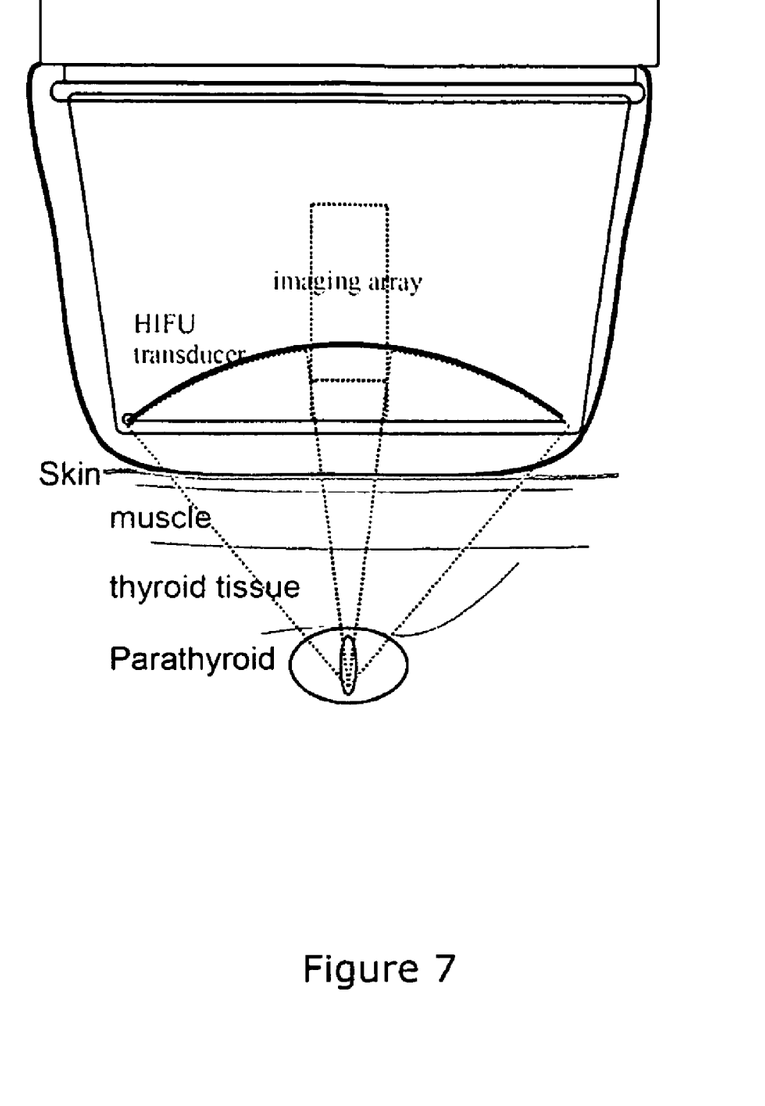

FIGS. 6 and 7 schematically show the geometry of a visualization and treatment unit VTU and a schematic arrangement of the VTU on the skin of patient. The VTU includes a ultrasound treatment transducer, a linear imaging array, sensors and electronics (not shown in detail).

As shown in FIG. 7, the transducer for generating the ultrasound has a concave shape with a certain radius of curvature in order to focus the ultrasound. The radius of curvature and thus the focal point is selected in such a way as to reach a treatment area including the parathyroid.

Typically and by way of example, the geometrical parameters of the VTU are chosen as follows:

| | |
|---|---|
| Radius of curvature of transducer | 38 mm |
| Distance from rim | 24.5 mm |
| Width of focus (6 dB) @ 3 MHz, cross × cross × along axis | 0.84 × 0.42 × 1.5 mm |
| Active Diameter | 56 mm |
| Width of Inactive area | 14.5 mm |
| External diameter at end of VTU | 60 mm |
| Acoustic frequency | 3 MHz |
| Maximum acoustic power | 70 W |

For parathyroids that are located deeper below the skin it is possible use a power transducer with a longer radius of curvature. For example if the transducer is built with a radius of curvature of 45 mm instead of 38 mm, the distance from rim becomes 35 mm and the focal zone is located at a distance such that parathyroids as deep as 35 mm can be treated.

While illustrative embodiments of the invention have been described above, it is, of course, understood that various modifications will be apparent to those of ordinary skill in the art. Such modifications are within the spirit and scope of the invention, which is limited and defined only by the appended claims.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

What is claimed is:

1. A method for treating disorders of thyroid and/or parathyroid with HIFU in a subject in need thereof comprising
   (i) identifying a treatment zone to which ultrasonic energy should be applied to, said treatment zone including at least a part of the parathyroid and
   (ii) directing high intensity focused ultrasound energy, with an energy level sufficient to cause tissue necrosis, towards said treatment zone
   the method comprising the further step of monitoring values of at least one blood level selected from the group of parathyroid hormone blood level, calcium blood level, blood phosphorous level, TSH hormone blood level, T3 hormone blood level and T4 hormone blood level of a patient.

2. A method for treating primary or secondary hyperparathyroidism comprising the steps of
   (i) identifying a treatment zone to which ultrasonic energy should be applied to, said treatment zone including at least a part of the parathyroid,
   (ii) directing high intensity focused ultrasound energy, with an energy level sufficient to cause tissue necrosis, toward said treatment zone, and
   (iii) monitoring a value of at least one blood level from the group of parathyroid hormone blood level, calcium blood level and blood phosphorus level.

3. A method according to claim 2 comprising positioning, for said step of directing high intensity focused ultrasound energy towards the treatment zone, a HIFU pulse generator to provide at least one HIFU pulse to a subject.

4. A method according to claim 3 wherein said step of directing high intensity focused ultrasound energy towards the treatment zone comprises providing of 10 to 100 pulses when treating secondary hyperparathyroidism.

5. A method according to claim 3 wherein said step of directing high intensity focused ultrasound energy towards the treatment zone comprises providing of 35 to 70 pulses when treating secondary hyperparathyroidism.

6. A method according to claim 3 wherein said step of directing high intensity focused ultrasound energy towards the treatment zone comprises delivering a total of between 4 kJ and 42 kJ of acoustic energy.

7. A method according to claim 3 wherein said step of directing high intensity focused ultrasound energy towards said treatment zone comprises delivering a total of between 7 kJ and 27 kJ, of acoustic energy.

8. A method according to claim 2 comprising positioning, for said step of identifying an ultrasound sensor to detect a position of a parathyroid to be treated in a subject.

9. A method according to claim 2 wherein only one of the four parathyroid glands is treated.

10. A method according to claim 2 wherein more than one of the four parathyroid glands are treated sequentially.

11. A method according to claim 2 comprising the further step of repeating the treatment steps of said identifying a treatment zone and of said directing high intensity focused ultrasound energy towards said treatment zone at least once.

12. A method according to claim 11 wherein said treatment steps are repeated at least one week after a previous treatment of primary or secondary hyper parathyroidism by directing high intensity focused ultrasound energy towards the treatment zone.

13. A method according to claim 11 wherein said treatment steps are repeated at the same treatment zone or at a treatment zone separated by 1 mm to 1 cm from said treatment zone.

14. A method according to claim 2 comprising further steps of repeating the treatment steps of said identifying a treatment zone and of said directing high intensity focused ultrasound energy towards said treatment zone at least once in dependence of a monitored value of said at least one blood level.

15. A method according to claim 14 comprising the further steps of repeating said treatment steps if value of the blood level of parathyroid hormones does not decrease by more than 30% after a previous treatment.

16. A method for modifying a parathyroid tissue comprising the steps of
   (i) identifying a treatment zone to which ultrasonic energy should be applied to, said treatment zone including at least a part of the parathyroid,
   (ii) directing high intensity focused ultrasound energy, with an energy level sufficient to cause tissue necrosis, towards the treatment zone, and
   (iii) monitoring a value of at least one blood level selected from the group of parathyroid hormone blood level, calcium blood level and blood phosphorus level.

17. A method for treating disorders of thyroid and/or parathyroid with HIFU in a subject in need thereof comprising the steps of:
   (i) identifying a treatment zone to which ultrasonic energy should be applied to, said treatment zone including at least a part of the parathyroid and
   (ii) directing high intensity focused ultrasound energy, with an energy level sufficient to cause tissue necrosis, towards said treatment zone,
   wherein said ultrasound energy is directed towards said treatment zone as a series of a least two pluses separated by pauses wherein said pauses are selected in such a way as to allow for prefocal tissue to return to normal temperature thereby avoiding or skin burn.

18. A method for treating a subject with HIFU, said method comprising steps of:
   (i) identifying a treatment zone to which ultrasonic energy should be applied and (ii) directing high intensity focused ultrasound energy toward said treatment zone,
wherein said ultrasound energy is directed towards said treatment zone as a series of at least two pulses separated by pauses, and
wherein the pauses are determined according to the following formula:

$$toff = \frac{F \cdot AcousticPower \cdot ton}{SkinTol \cdot \left[ TxdArea \cdot \left( \frac{TissueDepth}{FocusToRim} \right)^2 \right]} - ton$$

where:
toff=pause duration in seconds
ton=pulse duration in seconds
F=acoustic frequency in MHZ
Acoustic power=3 MHZ acoustic power delivered by the transducer during the HIFU pulse expressed in Watts
TissueDepth=thickness of tissues to go through, from the skin to the focal point over the lesion to be treated in mm
FocustoRim=distance from the focal point to the border of the active surface of the transducer projected over the ultrasound axis in mm.
TxdArea=cross section area of the transducer projection on the skin in $cm^2$
SkinTol=allowable average acoustic intensity through the skin in $W \times MHz/cm^2$.

19. A method according to claim 18, wherein the method is for treating disorders of thryoid and/or parathyroid and wherein the treatment zone includes at least a part of the parathyroid.

* * * * *